United States Patent [19]

Fünfschilling et al.

[11] Patent Number: 5,234,622
[45] Date of Patent: Aug. 10, 1993

[54] ALKENYLOXYPHENYLPYRIMIDINE DERIVATIVES AND LIQUID CRYSTALLINE MIXTURES CONTAINING SAME

[75] Inventors: Jürg Fünfschilling, Basel; Stephen Kelly, Möhlin, both of Switzerland

[73] Assignee: Hoffman-La Roche Inc., Nutley, N.J.

[21] Appl. No.: 898,768

[22] Filed: Jun. 9, 1992

[30] Foreign Application Priority Data

Jun. 14, 1991 [CH] Switzerland .......... 1771/91
Jun. 14, 1991 [CH] Switzerland .......... 1772/91
Oct. 16, 1991 [CH] Switzerland .......... 3035/91

[51] Int. Cl.$^5$ ............... C09K 19/34; C07D 239/02
[52] U.S. Cl. ............... 252/299.61; 252/299.1; 544/298
[58] Field of Search ............ 252/299.01, 299.61; 544/298

[56] References Cited

U.S. PATENT DOCUMENTS

| | | | |
|---|---|---|---|
| 5,013,476 | 5/1991 | Boller et al. | 252/299.61 |
| 5,043,093 | 8/1991 | Krause et al. | 252/299.61 |
| 5,064,566 | 11/1991 | Hopf et al. | 252/299.61 |
| 5,071,589 | 12/1991 | Dübel et al. | 252/299.61 |

FOREIGN PATENT DOCUMENTS

| | | |
|---|---|---|
| 3500909 | 1/1985 | Fed. Rep. of Germany. |
| 3515374 | 4/1985 | Fed. Rep. of Germany. |
| 3601452 | 1/1986 | Fed. Rep. of Germany. |
| 3731638 | 4/1989 | Fed. Rep. of Germany. |
| 2-62865 | 3/1990 | Japan. |

OTHER PUBLICATIONS

Oral Presentation at the 14th International Liquid Crystal conference on Jun. 21–26, 1992 in Pisa, Italy: 2-(-4-alkenyloxy phenyl)5-alkylpyrimidines: the relationship between position and nature (E/Z) of the double bond and transition temperatures by S. Kelly.
Derwent Abstract #87-207017/30 to DE 3,601,452.
Derwent Abstract #89-130804/18 to DE 3,731,638.

*Primary Examiner*—Robert L. Stoll
*Assistant Examiner*—Shean C. Wu
*Attorney, Agent, or Firm*—George M. Gould; George W. Johnston

[57] ABSTRACT

Compounds of the formula

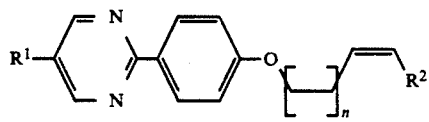

wherein $R^1$ signifies a straight-chain alkyl group with 7 to 10 carbon atoms; $R^2$ represents a straight-chain alkyl group with 1 to 8 carbon atoms; and n signifies either 1, 2 or 3, their preparation, liquid crystalline mixtures which contain these compounds and their use for electro-optical purposes.

11 Claims, No Drawings

ALKENYLOXYPHENYLPYRIMIDINE DERIVATIVES AND LIQUID CRYSTALLINE MIXTURES CONTAINING SAME

FIELD OF THE INVENTION

The present invention is concerned with alkenyloxyphenylpyrimidine derivatives, liquid crystalline mixtures which contain these compounds and their use for electro-optical purposes.

BACKGROUND OF THE INVENTION

Liquid crystals are used primarily as dielectrics in indicating devices, since the optical properties of such substances can be influenced by an applied voltage. Electro-optical devices based on liquid crystals are well-known to a person skilled in the art and can be based on various effects. Examples of such devices are cells having dynamic scattering, DAP cells (deformation of aligned phases), SSF cells (surface stabilized ferroelectric), DHF cells (deformed helix ferroelectric) or SBF cells (short-pitch bistable ferroelectric).

The liquid crystal materials must have good chemical and thermal stability and good stability towards electric fields and electromagnetic radiation. Further, the liquid crystal materials should have low viscosity and in the cells should give short response times and high contrast. Furthermore, at usual operating temperatures of about −30° C. to about +80° C., especially of about −20° C. to about +60° C., they should have a suitable mesophase, for example, a broad smectic mesophase for the cells referred to above.

Moreover, since liquid crystals are usually used as mixtures of several components, it is important that the components have a good miscibility with one another.

SUMMARY OF THE INVENTION

The invention pertains to alkenyloxyphenylpyrimidine derivatives of the formula:

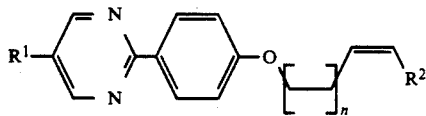

I wherein $R^1$ is a straight-chain alkyl group of 7 to 10 carbon atoms; $R^2$ is a straight-chain alkyl group of 1 to 8 carbon atoms; and n is the integer 1, 2 or 3.

The invention also pertains to liquid crystalline mixtures having at least two components, at least one of which is a compound of formula I.

DETAILED DESCRIPTION OF THE INVENTION

The present invention relates to compounds of the formula

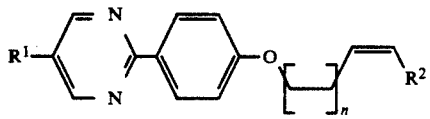

I wherein $R^1$ is a straight-chain alkyl group with 7 to 10 carbon atoms; $R^2$ is a straight-chain alkyl group with 1 to 8 carbon atoms; and n is the integer 1, 2 or 3.

It has surprisingly been found that the compounds in accordance with the invention have extremely favorable mesophases for ferroelectric applications. A significant lowering of the melting point is often brought about by the introduction of the cis double-bond in the 3-, 5- or 7-position of the alkoxy side-chain of the compounds of formula I and this leads to comparatively broad smectic mesophases. The smectic mesophases of the compounds have a surprisingly low viscosity which leads to rapid switching times. By mixing these compounds with known basic components for ferroelectric mixtures the crystallisation of individual components is significantly suppressed and this leads to a comparatively broad mesophase of the mixture and an excellent low temperature behavior. Moreover, mixtures containing the compounds in accordance with the invention have an excellent multiplex behavior in SBF cells.

The term "straight-chain alkyl group with 7 to 10 carbon atoms" denotes heptyl, octyl, nonyl and decyl. The term "straight-chain alkyl group with 1 to 8 carbon atoms" denotes methyl, ethyl, propyl, butyl, pentyl, hexyl, heptyl and octyl.

Compounds of formula I in which $R^1$ is heptyl, octyl or nonyl, $R^2$ is ethyl, propyl, butyl, pentyl or hexyl and n is 1 or 2 are preferred.

Particularly preferred compounds of general formula I are compounds in which $R^1$ is nonyl, n is 1 and $R^2$ is butyl, pentyl or hexyl, these being examples of the preferred compounds:

5-nonyl-2-(4-[(3Z)-octenyloxy]phenyl)pyrimidine;
5-nonyl-2-(4-[(3Z)-nonenyloxy]phenyl)pyrimidine;
5-nonyl-2-(4-[(3Z)-decenyloxy]phenyl)pyrimidine;

as well as compounds of formula I in which $R^1$ is nonyl, n is 2 and $R^2$ is ethyl, propyl or butyl; these being examples of the preferred compounds:

5-nonyl-2-(4-[(5Z)-octenyloxy]phenyl)pyrimidine;
5-nonyl-2-(4-[(5Z)-nonenyloxy]phenyl)pyrimidine;
5-nonyl-2-(4-[(5Z)-decenyloxy]phenyl)pyrimidine.

These compounds are distinguished by an especially broad smectic mesophase range with a low melting point.

The compounds in accordance with the invention can be prepared in a manner known per se, e.g. from a 4-(5-alkylpyrimidin-2-yl)phenol and the corresponding alcohol which is unsaturated in the 3-, 5- or 7-position. The reaction is effected in the presence of diethyl azodicarboxylate and triphenylphosphine in tetrahydrofuran or another suitable solvent such as e.g. hexane. The cis-alcohols used as starting materials are to some extent commercially available or can be prepared by a Wittig reaction of commercially available aldehydes and a Wittig reagent (alkyltriphenylphosphonium chloride). Preferably, however, the cis-alcohols are prepared by catalytically hydrogenating the corresponding alkynol in the presence of a Lindlar catalyst.

The compounds of formula I can be used in the form of mixtures with one another and/or with other liquid crystal components. However, the compounds of formula I are preferably used in mixtures with other liquid crystal components.

The liquid crystalline mixtures in accordance with the invention contain at least two components of which at least one component is a compound of formula I. A second component and, optionally, additional components can be further compounds of formula I or other liquid crystalline compounds. However, in each case at least one chiral component must be present in the mixture. Insofar as one of the liquid crystalline compounds used is not already itself chiral, a chiral dopant must be added.

Such liquid crystal components are preferably achiral compounds of the formulas

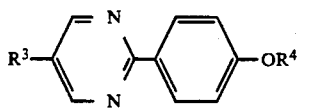   II

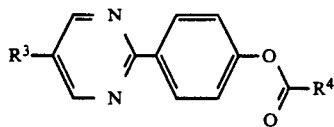   III

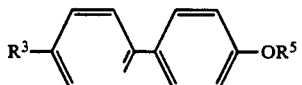   IV

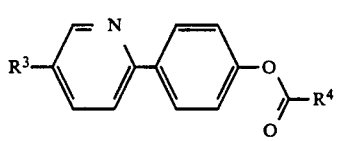   V or dopants of the formulas

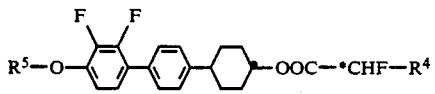   VI

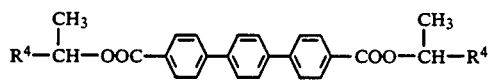   VII wherein $R^3$ is alkyl or alkoxy, $R^4$ is alkyl and $R^5$ is alkyl or alkenyl.

The term "alkyl" in connection with the compounds of formulas II to VII embraces unbranched or branched alkyl groups with 1 to 15 carbon atoms, preferably unbranched alkyl groups with 1-12 carbon atoms such as methyl, ethyl, propyl, butyl, pentyl, hexyl, heptyl, octyl, nonyl, decyl, undecyl, dodecyl.

The term "alkoxy" embraces ether groups in which the alkyl residue is as defined hereinbefore.

The term "alkenyl" embraces alkenyl groups with 2 to 15 carbon atoms such as 2E-alkenyl, 3Z-alkenyl, 4E-alkenyl and alkenyls with a terminal double bond. The terms "2E-alkenyl", "3Z-alkenyl" and "4E-alkenyl" embrace unbranched alkenyl groups with 3 to 15, 4 to 15 and, respectively, 5 to 15 carbon atoms in which the double bond is present in the 2, 3 and, respectively, 4 position, with E and Z denoting the configuration of the double bond. Such groups are, for example, allyl, 2E-butenyl, 2E-pentenyl, 2E-hexenyl, 2E-heptenyl, 2E-octenyl, 2E-nonenyl, 2E-decenyl, 3-butenyl, 3Z-pentenyl, 3Z-hexenyl, 3Z-heptenyl, 3Z-octenyl, 3Z-nonenyl, 3Z-decenyl, 4-pentenyl, 4E-hexenyl, 4E-heptenyl, 4E-octenyl, 4E-nonenyl, 4E-decenyl, 5-hexenyl, 6-heptenyl, 7-octenyl, 8-nonenyl, 9-decenyl, 10-undecenyl, 11-dodecenyl and the like.

Having regard to the good solubility of the compounds of formula I and having regard to their good miscibility with one another, the content of compounds formula I in the mixtures in accordance with the invention can be relatively high and can be up to about 85 wt. %. However, a content of about 1-50, especially 5-30, wt. % of compounds of formula I is generally preferred.

The manufacture of the liquid crystalline mixtures and of the electro-optical devices can be effected in a manner known per se.

The invention is illustrated in more detail by the following Examples. In the Examples, C signifies a crystalline phase, N signifies a nematic phase, S signifies a smectic phase and I signifies the isotropic phase. The notations, e.g., (C-S$_C$) indicate the phase transition temperature points from crystalline to smectic C.

EXAMPLE 1

5-Nonyl-2-(p-hydroxyphenyl)pyrimidine (0.5 g) was dissolved in 25 ml of tetrahydrofuran in a flask at room temperature overnight together with 0.22 g of 3-(Z)-nonen-1-ol, 0.29 g of diethyl azodicarboxylate and 0.44 g of triphenylphosphine. The solution was concentrated, the residue was suspended with 50 ml of hexane and filtered. The filtrate was concentrated. Chromatographic purification of the residue on 25 g of silica gel with hexane/ethyl acetate (9:1 vol %) and subsequent recrystallization from 5 ml of ethyl alcohol at −25° C. gave 0.38 g of pure 5-nonyl-2-(4-[(3Z)-nonenyloxy]-phenyl)pyrimidine with a melting point (m.p.) (C-S$_C$) of 6° C., S$_C$-S$_A$ 37° C. and a clearing point (cl.p.) (S$_A$-I) of 51° C.

The following compounds are prepared in an analogous manner:

5-Heptyl-2-(4-[(3Z)-hexenyloxy]phenyl)pyrimidine, m.p. (C-S$_A$) 43° C., S$_A$-N 45° C., cl.p. (N-I) 48° C.;

5-heptyl-2-(4-[(3Z)-octenyloxy]phenyl)pyrimidine, m.p. (C-S$_A$) 28° C., S$_A$-N 43° C., cl.p. (N-I) 44° C.;

5-heptyl-2-(4-[(3Z)-nonenyloxy]phenyl)pyrimidine, m.p. (C-S$_C$) 25° C., S$_C$-S$_A$ (6° C.), cl.p. (S$_A$-I) 40° C.;

5-heptyl-2-(4-[(3Z)-decenyloxy]phenyl)pyrimidine;

5-heptyl-2-(4-[(3Z)-undecenyloxy]phenyl)pyrimidine;

5-heptyl-2-(4-[(3Z)-dodecenyloxy]phenyl)pyrimidine;

5-heptyl-2-(4-[(5Z)-octenyloxy]phenyl)pyrimidine, m.p. (C-S$_C$) 2° C., S$_C$-S$_A$ 24° C., S$_A$-N 47° C., cl.p. (N-I) 53° C.;

5-heptyl-2-(4-[(5Z)-nonenyloxy]phenyl)pyrimidine;

5-heptyl-2-(4-[(5Z)-decenyloxy]phenyl)pyrimidine;

5-heptyl-2-(4-[(5Z)-undecenyloxy]phenyl)pyrimidine;

5-heptyl-2-(4-[(5Z)-dodecenyloxy]phenyl)pyrimidine;

5-heptyl-2-(4-[(7Z)-nonenyloxy]phenyl)pyrimidine;

5-heptyl-2-(4-[(7Z)-decenyloxy]phenyl)pyrimidine;

5-heptyl-2-(4-[(7Z)-undecenyloxy]phenyl)pyrimidine;

5-heptyl-2-(4-[(7Z)-dodecenyloxy]phenyl)pyrimidine;

5-octyl-2-(4-[(3Z)-hexenyloxy]phenyl)pyrimidine, m.p. (C-S$_C$) 42° C., S$_C$-S$_A$ 32° C., cl.p. (S$_A$-I) 47° C.;

5-octyl-2-(4-[(3Z)-octenyloxy]phenyl)pyrimidine, m.p. (C-S$_C$) 10° C., S$_C$-S$_A$ 38° C., cl.p. (S$_A$-I) 53° C.;

5-octyl-2-(4-[(3Z)-nonenyloxy]phenyl)pyrimidine, m.p. (C-S$_C$) 12° C., S$_C$-S$_A$ 27° C., cl.p. (S$_A$-I) 42° C.;

5-octyl-2-(4-[(3Z)-decenyloxy]phenyl)pyrimidine;

5-octyl-2-(4-[(3Z)-undecenyloxy]phenyl)pyrimidine;

5-octyl-2-(4-[(3Z)-dodecenyloxy]phenyl)pyrimidine;

5-octyl-2-(4-[(5Z)-octenyloxy]phenyl)pyrimidine, m.p. (C-S$_C$) 25° C., S$_C$-S$_A$ 34° C., cl.p. (S$_A$-I) 45° C.;

5-octyl-2-(4-[(5Z)-nonenyloxy]phenyl)pyrimidine;

5-octyl-2-(4-[(5Z)-decenyloxy]phenyl)pyrimidine;

5-octyl-2-(4-[(5Z)-undecenyloxy]phenyl)pyrimidine;

5-octyl-2-(4-[(5Z)-dodecenyloxy]phenyl)pyrimidine;

5-octyl-2-(4-[(7Z)-nonenyloxy]phenyl)pyrimidine;

5-octyl-2-(4-[(7Z)-decenyloxy]phenyl)pyrimidine;

5-octyl-2-(4-[(7Z)-undecenyloxy]phenyl)pyrimidine;

5-octyl-2-(4-[(7Z)-dodecenyloxy]phenyl)pyrimidine;
5-nonyl-2-(4-[(3Z)-hexenyloxy]phenyl)pyrimidine, m.p. (C-$S_C$) 58° C., $S_C$-$S_A$ 41° C., cl.p. ($S_A$-I) (56° C.);
5-nonyl-2-(4-[(3Z)-octenyloxy]phenyl)pyrimidine, m.p. (C-$S_C$) 24° C., $S_C$-$S_A$ 43° C., cl.p. ($S_A$-I) 54° C.;
5-nonyl-2-(4-[(3Z)-decenyloxy]phenyl)pyrimidine;
5-nonyl-2-(4-[(3Z)-undecenyloxy]phenyl)pyrimidine;
5-nonyl-2-(4-[(3Z)-dodecenyloxy]phenyl)pyrimidine;
5-nonyl-2-(4-[(5Z)-octenyloxy]phenyl)pyrimidine, m.p. (C-$S_C$) 24° C., $S_C$-$S_A$ 45° C., cl.p. ($S_A$-I) 61° C.;
5-nonyl-2-(4-[(5Z)-nonenyloxy]phenyl)pyrimidine;
5-nonyl-2-(4-[(5Z)-decenyloxy]phenyl)pyrimidine;
5-nonyl-2-(4-[(5Z)-undecenyloxy]phenyl)pyrimidine;
5-nonyl-2-(4-[(5Z)-dodecenyloxy]phenyl)pyrimidine;
5-nonyl-2-(4-[(7Z)-nonenyloxy]phenyl)pyrimidine;
5-nonyl-2-(4-[(7Z)-decenyloxy]phenyl)pyrimidine;
5-nonyl-2-(4-[(7Z)-undecenyloxy]phenyl)pyrimidine;
5-nonyl-2-(4-[(7Z)-dodecenyloxy]phenyl)pyrimidine.

EXAMPLE 2

In order to investigate the properties of the compounds of formula I, a basic mixture was prepared and in each case admixed with 15% of a compound of formula I. The phase transition temperatures of these mixtures were determined, the crystallization temperature $T_c$ was determined from conductivity data. The switching times were measured at 25° C. (10 Vpp/μ, time from the start of the pulse to maximum current). The measured values are compiled in Tables 1 and 2.

Basic mixture 16 wt. % of p-[trans-4-{[(R)-2-fluorohexanoyl]oxy}cyclohexyl]phenyl 2,3-difluoro-4-(octyloxy)benzoate;
24 wt. % of 2-[p-(hexyloxy)phenyl]-5-nonylpyrimidine;
24 wt. % of 2-[p-(nonyloxy)phenyl]-5-nonylpyrimidine;
12 wt. % of 2-[p-(nonyloxy)phenyl]-5-heptylpyrimidine;
12 wt. % of 2-[p-(heptyloxy)phenyl]-5-octylpyrimidine;
12 wt. % of 2-[p-(decyloxy)phenyl]-5-octylpyrimidine.

TABLE 1

15 wt. % of [structure] + 85 wt. % of basic mixture

| n | C/$S_X$–$S_C*$ °C. | $S_C*$–$S_A$ °C. | $S_A$–N °C. | N–I °C. | Switching time μsec |
|---|---|---|---|---|---|
| 7 | −11.7 | 52.3 | 62.3 | 68.2 | 115 |
| 8 | −4.4 | 55.7 | 63.8 | 69.9 | 110 |
| 9 | −5.9 | 55.3 | 65.2 | 69.0 | 100 |

TABLE 2

15 wt. % of [structure] + 85 wt. % of basic mixture

| n | C/$S_X$–$S_C*$ °C. | $S_C*$–$S_A$ °C. | $S_A$–N °C. | N–I °C. | Switching time μsec |
|---|---|---|---|---|---|
| 7 | −8.2 | 53.9 | 62.8 | 69.6 | 112 |
| 8 | −6.0 | 54.6 | 62.8 | 68.5 | 102 |
| 9 | −5.0 | 57.1 | 66.6 | 70.7 | 110 |

What is claimed is:

1. A compound of the formula

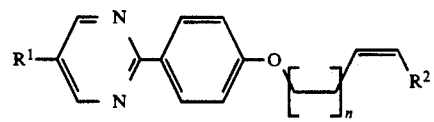

wherein $R^1$ is a straight-chain alkyl group with 7 to 10 carbon atoms; $R^2$ is a straight-chain alkyl group with 1 to 8 carbon atoms; and n is the integer 1 or 2.

2. The compound according to claim 1, wherein $R^1$ is heptyl, octyl or nonyl.

3. The compound according to claim 1, wherein n is 1 and $R^2$ is butyl, pentyl or hexyl.

4. The compound according to claim 1, wherein n is 2 and $R^2$ is ethyl, propyl or butyl.

5. The compound according to claim 1, which is 5-nonyl-2-(4-[(3Z)-octenyloxy]phenyl)-pyrimidine.

6. The compound according to claim 1, which is 5-nonyl-2-(4-[(3Z)-nonenyloxy]phenyl)-pyrimidine.

7. The compound according to claim 1, which is 5-nonyl-2-(4-[(3Z)-decenyloxy]phenyl)-pyrimidine.

8. The compound according to claim 1, which is 5-nonyl-2-(4-[(5Z)-octenyloxy]phenyl)-pyrimidine.

9. The compound according to claim 1, which is 5-nonyl-2-(4-[(5Z)-nonenyloxy]phenyl)-pyrimidine.

10. The compound according to claim 1, which is 5-nonyl-2-(4-[(5Z)-decenyloxy]phenyl)-pyrimidine.

11. A liquid crystalline mixture having at least two components, wherein at least one component is a compound according to claim 1.

* * * * *